(12) United States Patent
Tsai

(10) Patent No.: US 7,528,108 B2
(45) Date of Patent: May 5, 2009

(54) COMPOSITIONS AND METHODS FOR TREATING OR PREVENTING OVERWEIGHT OR OBESITY WITH ZINC-CHARGED PROTEIN FRAGMENTS

(75) Inventor: David Men Hwei Tsai, Diamond Bar, CA (US)

(73) Assignee: Ambryx Biotechnology, Inc., Riverside, CA (US)

( * ) Notice: Subject to any disclaimer, the term of this patent is extended or adjusted under 35 U.S.C. 154(b) by 0 days.

(21) Appl. No.: 11/411,603

(22) Filed: Apr. 25, 2006

(65) Prior Publication Data

US 2007/0004617 A1 Jan. 4, 2007

Related U.S. Application Data

(63) Continuation-in-part of application No. 11/315,810, filed on Dec. 22, 2005, now abandoned, which is a continuation-in-part of application No. 11/114,792, filed on Apr. 26, 2005, now abandoned.

(51) Int. Cl.
*A61K 38/40* (2006.01)
*A61K 49/00* (2006.01)

(52) U.S. Cl. ............... 514/6; 514/12; 530/300; 530/400; 424/9.1

(58) Field of Classification Search ............ 514/6, 514/12; 530/400, 300; 424/9.1
See application file for complete search history.

(56) References Cited

U.S. PATENT DOCUMENTS

| 4,009,265 | A | * | 2/1977 | Howard ............ 514/21 |
|---|---|---|---|---|
| 5,840,851 | A | | 11/1998 | Plomer et al. |
| 5,994,298 | A | | 11/1999 | Tsai et al. |
| 6,258,779 | B1 | | 7/2001 | Tsai |
| 6,720,311 | B2 | | 4/2004 | Tsai |
| 6,737,402 | B2 | | 5/2004 | Tsai |
| 7,193,040 | B2 | | 3/2007 | Tsai |
| 7,238,662 | B2 | | 7/2007 | Tsai |
| 2002/0094349 | A1 | | 7/2002 | Tsai |
| 2003/0118662 | A1 | | 6/2003 | Bastian et al. |
| 2003/0165574 | A1 | | 9/2003 | Ward et al. |
| 2003/0203008 | A1 | | 10/2003 | Gunasekaran |
| 2005/0106218 | A1 | | 5/2005 | Ward et al. |
| 2005/0238694 | A1 | * | 10/2005 | Gerhardt et al. ......... 424/439 |

OTHER PUBLICATIONS

Hurley, W.L. "Milk proteins and protein synthesis," Internet posting at http://classes.aces.uiuc.edu/AnSci308, originally accessed Dec. 7, 2005.
Yu, C.L., Tsai, M.H. (David), "Fetal fetuin selectively induces apoptosis in cancer cell lines and shows anti-cancer activity in tumor animal models," *Cancer Lett.*, 166(2):173-84 (May 26, 2001).
Yu, C.L., Tsai, M.H. (David), "Embryonic apoptosis-inducing proteins exhibited anticancer activity in vitro and in vivo," *Anticancer Res.*, 21(3B):1839-56 (May-Jun. 2001).
Written Opinion from PCT/US06/15644, Aug. 8, 2007, Ambryx Biotechnology, Inc.
International Preliminary Report on Patentability, Oct. 30, 2007, Ambryx Biotechnology, Inc.

* cited by examiner

*Primary Examiner*—Chih-Min Kam
(74) *Attorney, Agent, or Firm*—Jones Day

(57) ABSTRACT

Compositions and methods for treating or preventing, for example, overweight or obesity are provided. Compositions provided comprise zinc-charged, protease digested serum or milk proteins. Compositions are administered in a therapeutically effective amount to treat or prevent, for example, overweight or obesity.

33 Claims, 10 Drawing Sheets

Control: Adipocyte with oil droplets

Figure 1:
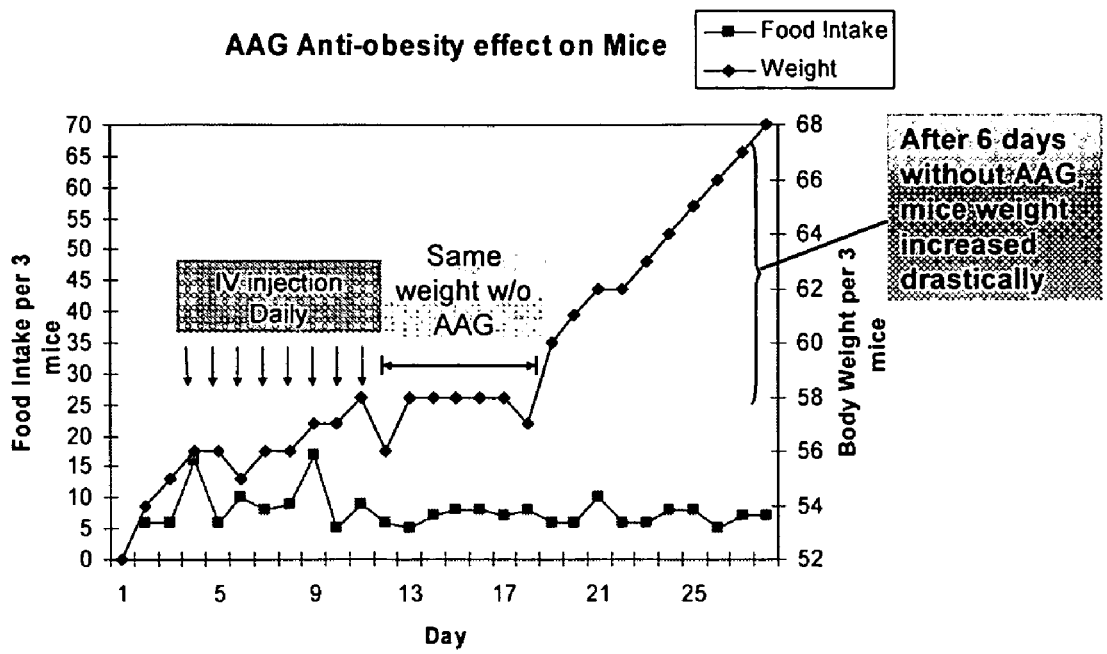

Apoptosis is visible within 6-8 hrs.

Oil Droplets containing triglyceride

Control: Adipocyte forms oil droplets

Peptides inhibited adipocytes from forming oil droplets

COMPOSITIONS AND METHODS FOR TREATING OR PREVENTING OVERWEIGHT OR OBESITY WITH ZINC-CHARGED PROTEIN FRAGMENTS

The instant application is a continuation-in-part of U.S. application Ser. No. 11/315,810, filed Dec. 22, 2005, now abandoned, which is a continuation-in-part of U.S. application Ser. No. 11/114,792, filed Apr. 26, 2005, now abandoned. The instant application claims priority under 35 U.S.C. § 120 to each of the above applications, and the instant application incorporates each of the above applications by reference in their entireties.

1. FIELD OF THE INVENTION

The invention relates to compositions and methods for treating or preventing obesity or overweight. In particular, the invention discloses preparing and administering to a patient a mixture of zinc-charged, protease digested proteins derived, for example, from serum or milk.

2. BACKGROUND OF THE INVENTION

Obesity is a serious health epidemic. According to the Centers for Disease Control and Prevention (CDC) and the National Health and Nutrition Examination Survey (NHANES) 1999-2000, an estimated 64 percent of U.S. adults are either overweight or obese (overweight means having a body mass index (BMI) of 25 or greater, obese means having a BMI of 30 or greater), and that number appears to be growing. In the past 15 years, the prevalence of obesity among adults has increased by over 30 percent. Even more startling, over the past two decades, it has increased 100 percent in children and adolescents. Overweight and obese individuals are at increased risk for physical ailments such as high blood pressure, hypertension, high blood cholesterol levels, diabetes, insulin resistance, glucose intolerance, coronary heart disease and even psychological disorders, such as depression and eating disorders. (National Institutes of Health: Clinical Guidelines on the Identification, Evaluation, and Treatment of Overweight and Obesity in Adults, 1998, Bethesda, Md.: Department of Health and Human Services, National Institutes of Health, National Heart, Lung, and Blood Institute; Mokdad et al., 2001, *JAMA* 289:76-79).

When people become obese, two things happen to the fat cells (adipocytes) in their body: both the volume and the number of these cells increase. The total number of adipocytes in the human body increases only when a person gains a large amount of weight. The lesser fluctuations in a person's weight are usually associated with an incremental increase or decrease in the average size of the fat cells. However, there is a maximum size to which adipocytes can grow. With significant weight gain, new adipocytes are created from fibroblasts. Unfortunately, when a person loses a substantial amount of weight by dieting, the adipocytes simply shrink in size but do not necessarily diminish in number. The fact that the fat cell number remains the same in a person losing the weight explains the difficulty of losing weight and maintaining the achieved weight loss. These goals may be attained more efficiently by reducing the number of fat cells.

Current anti-obesity treatments focus on suppressing appetite through medication, restricting food intake, or, in the most radical approach, weight loss surgery. The popular appetite suppressant drugs can be divided into two types: noradrenergic agents like phenylpropanolamine (Acutrim, Dexatrim), which affect the brain's appetite center, and serotonergic agents like fenfluramine and dexfenfluramine, which affect the brain's satiety center. (Williamson, 1999, *JAMA* 281:278-279). However, research has shown that the neurophysiology of feeding behavior is very complex, making appetite suppression difficult to achieve. At the same time, fenfluramine and its derivatives have been associated with extremely harmful side effects, necessitating the ban on these substances. Patients attempting to restrict food intake often have difficulty completing the weight loss programs and are prone to relapse as they return to the old eating habits. The extra food quickly gets converted into fat that refills the adipocytes, that shrunk through weight loss. The surgery reducing the size of the stomach dramatically limits food intake. However, this surgery has its own side effects and is recommended only for severely obese individuals. During liposuction procedures the fat is removed only from certain areas of the body. As a result, the adipocytes remaining in other areas, such as neck and forearms, uptake a disproportional amount of fat, creating an unsightly appearance.

It is therefore desirable to provide a non-invasive weight loss treatment that would act by reducing the number of fat cells. It would be especially advantageous if the fat cells throughout the body (and not just in a limited area) could be targeted.

3. SUMMARY OF THE INVENTION

The present invention is based, in part, on the discovery of compositions and methods that are useful for reducing weight gain and even for effecting weight loss in a subject in need thereof. It is believed, without limiting any scope of invention, that compositions and methods of the invention are capable of inducing apoptosis of adipocytes in a subject. It is also believed, without limiting any scope of invention, that compositions and methods of the invention are capable of modulating insulin receptor activity in a subject. The examples below demonstrate that compositions and methods of the invention are effective to reduce the weight of a human subject.

In one aspect, the present invention provides compositions useful for methods described herein. In certain embodiments, the compositions are in the form of pharmaceutical unit dosages. In certain embodiments, the compositions are in the form of nutraceutical unit dosages. In certain embodiments, the compositions are in the form of dietary supplements or food additives or food compositions. In certain embodiments, the compositions of the invention comprise zinc-charged, protease digested serum or milk proteins. In certain embodiments, the protease is papain. In certain embodiments, the serum or milk proteins are selected from the group consisting of α-2-HS-glycoprotein, α-1-acid glycoprotein, α-1-antitrypsin, albumin, transferrin and α-fetoprotein.

In another aspect, the present invention provides methods of treating a subject with one or more compositions of the invention. In certain embodiments, the present invention provides methods of treating or preventing obesity. In certain embodiments, the present invention provides methods of treating or preventing overweight. In certain embodiments, the present invention provides methods of reducing weight gain. In certain embodiments, the present invention provides methods of inducing weight loss. The methods comprise the step of administering an effective amount of a composition of the invention to the subject. In preferred embodiments, the present invention provides methods of treating or preventing overweight or obesity in a human.

In another aspect, the present invention provides methods of using a composition described herein to induce apoptosis of an adipocyte with a composition described herein. The methods comprise the step of contacting the adipocyte with a composition of the invention. The cell can be any adipocyte including an adipocyte in vivo, in vitro or ex vivo. In certain embodiments, the adipocyte is in a subject. In certain embodiments, the adipocyte is in a human.

In a further aspect, the present invention provides a method and composition for treating obesity that directly reduces the number of fat cells through apoptosis. This method differs from the conventional methods of weight reduction, including suppressing appetite, limiting food intake or removing fat cells from a single area of the body. The compositions of the invention comprise protease digested, zinc-charged protein fragments effective for treating or preventing obesity or overweight in a subject in need thereof.

In another aspect, the provided herein are methods of preparing the compositions of the invention.

4. BRIEF DESCRIPTION OF THE DRAWINGS

Figure 2:
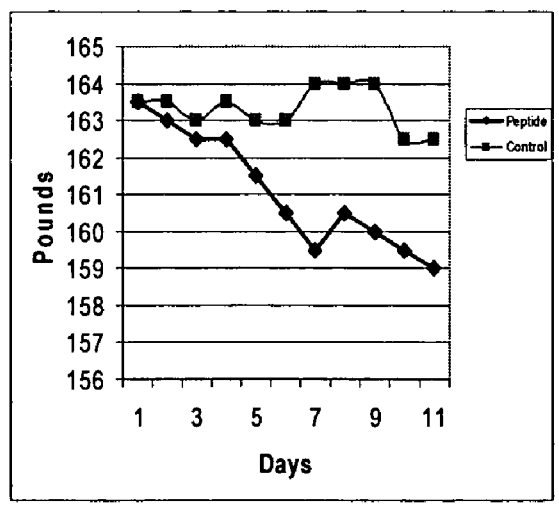
Figure 3A:
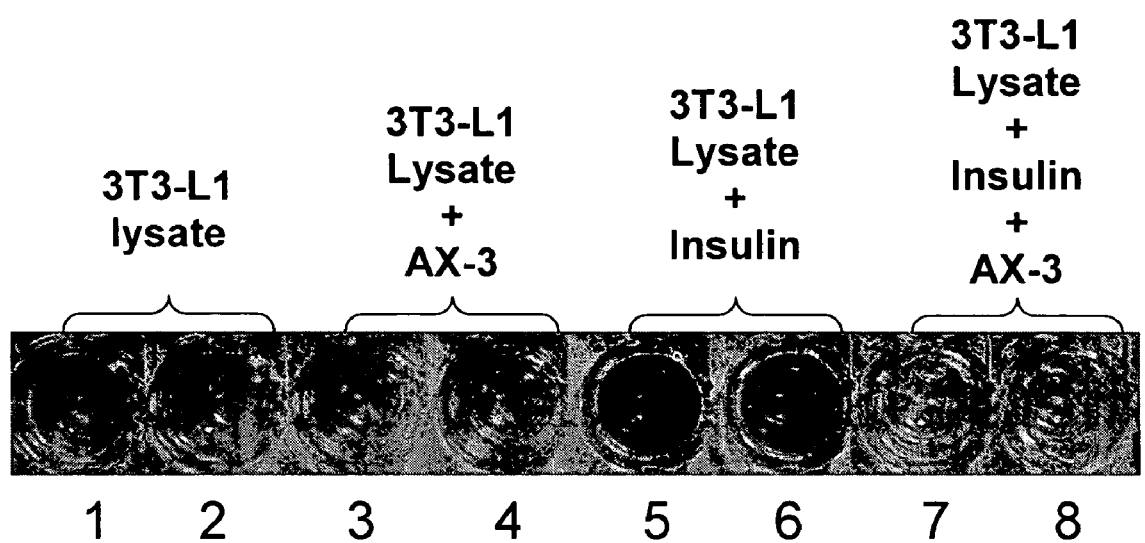
Figure 3B:
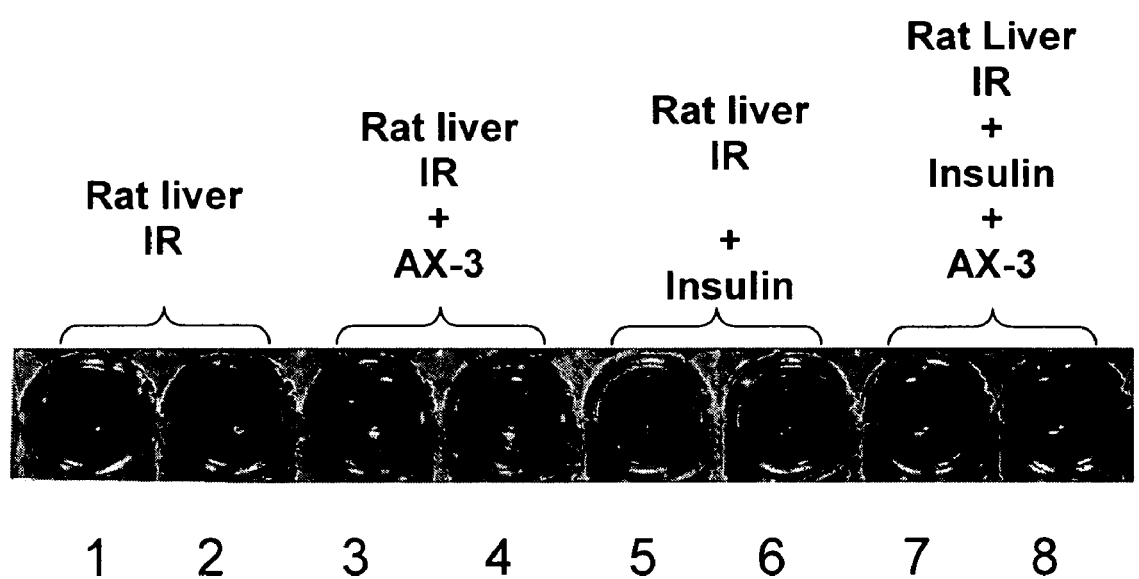
Figure 4A:
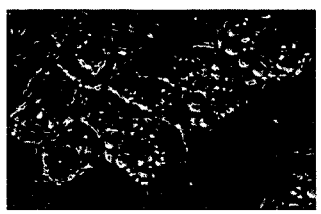
Figure 4A:
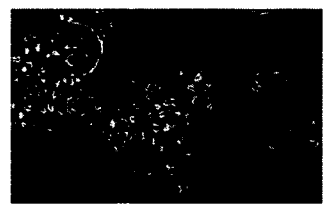
Figure 4B:
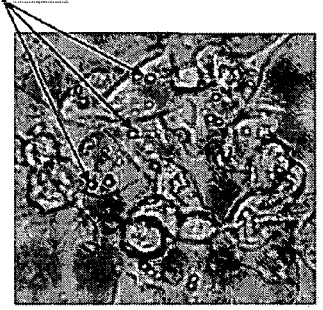
Figure 4B:
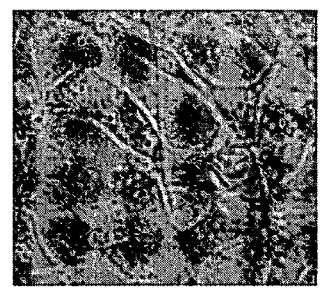
Figure 5:
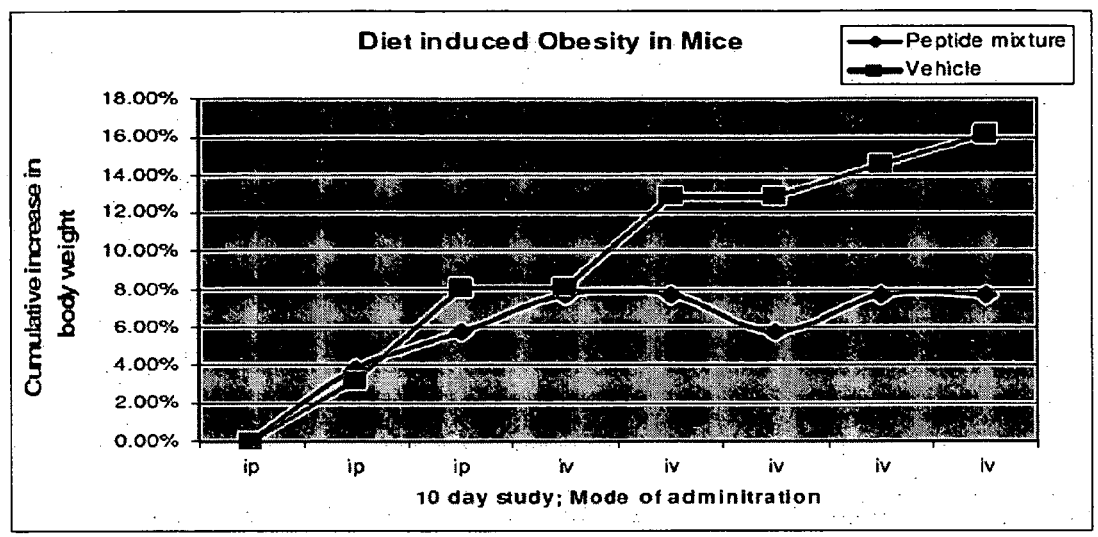
Figure 6:
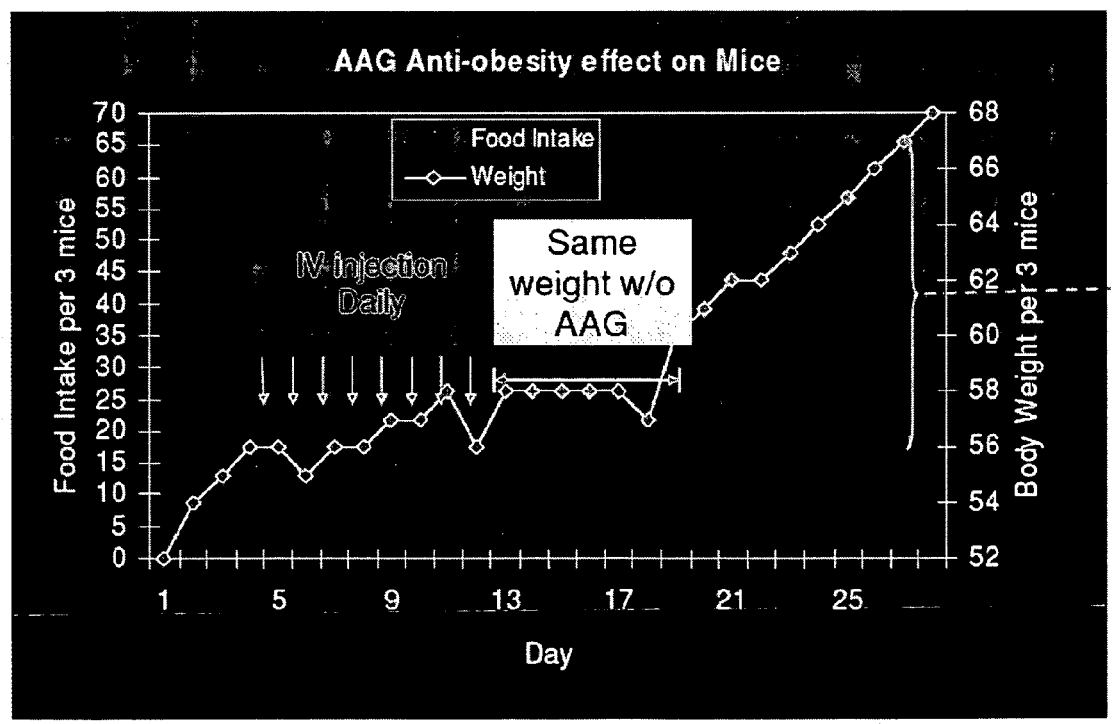
Figure 7:
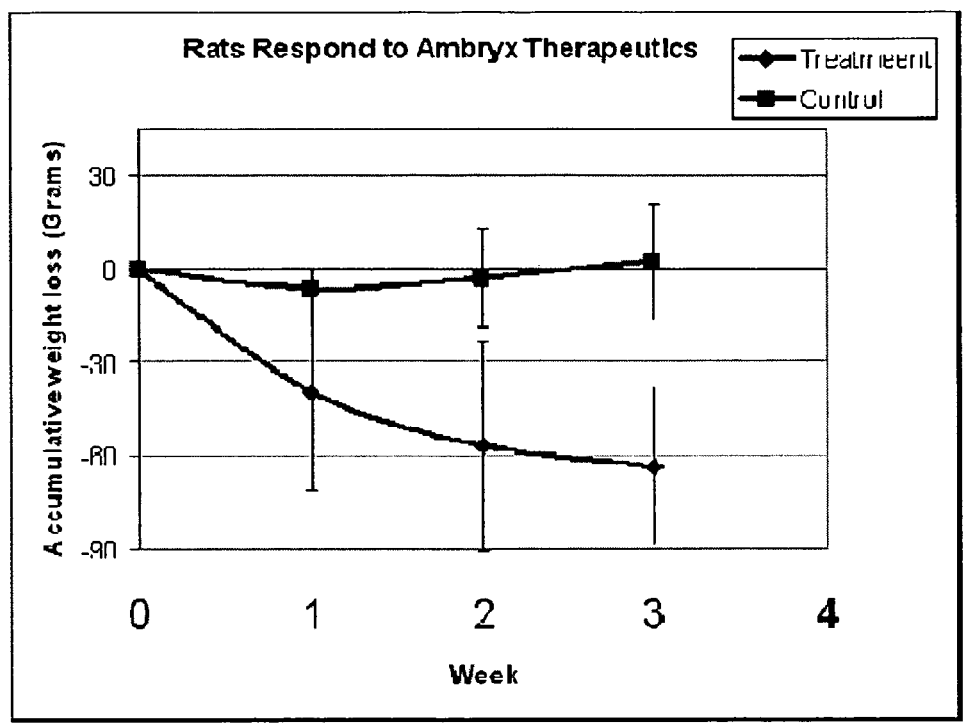
Figure 8:
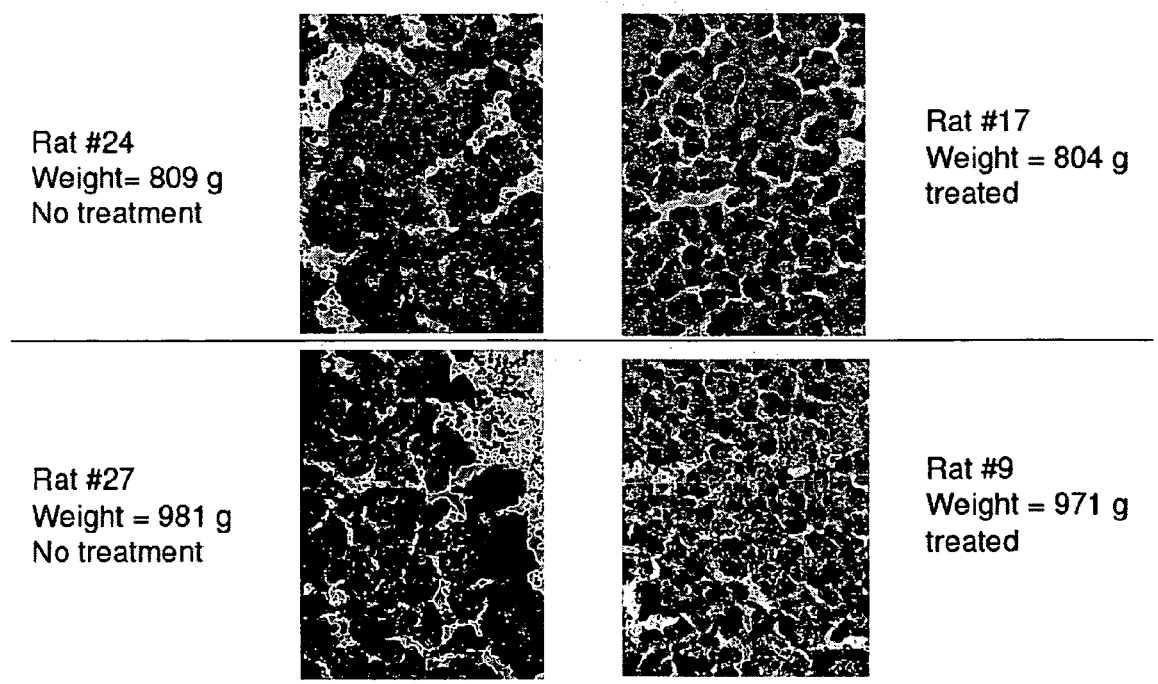
Figure 9:
Figure 10:
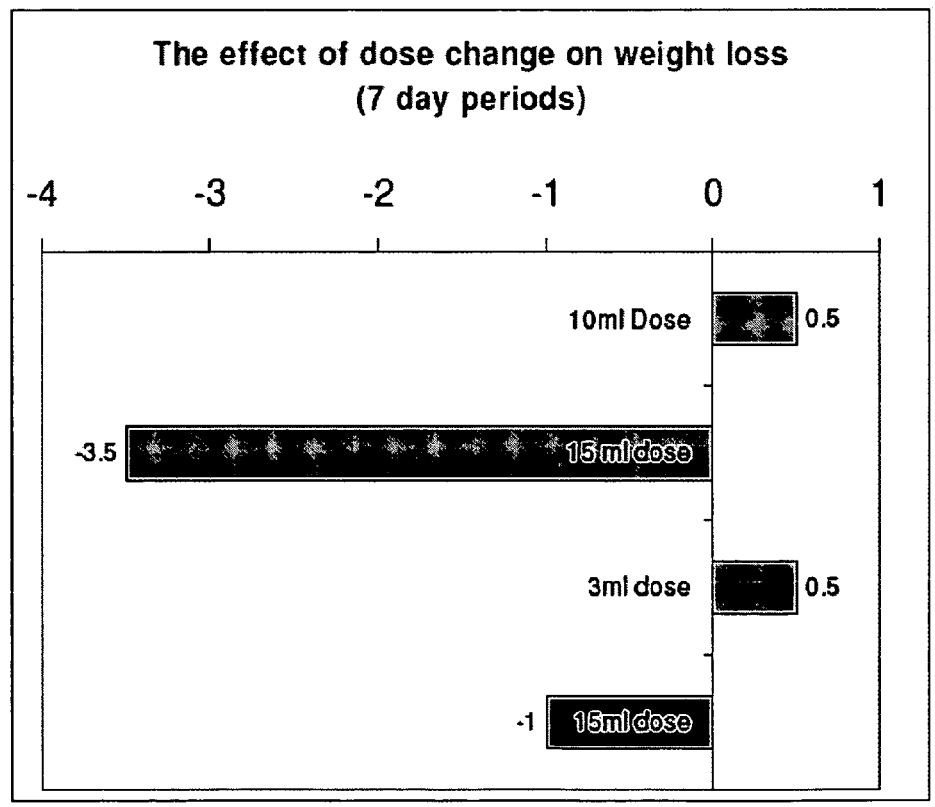
Figure 11:
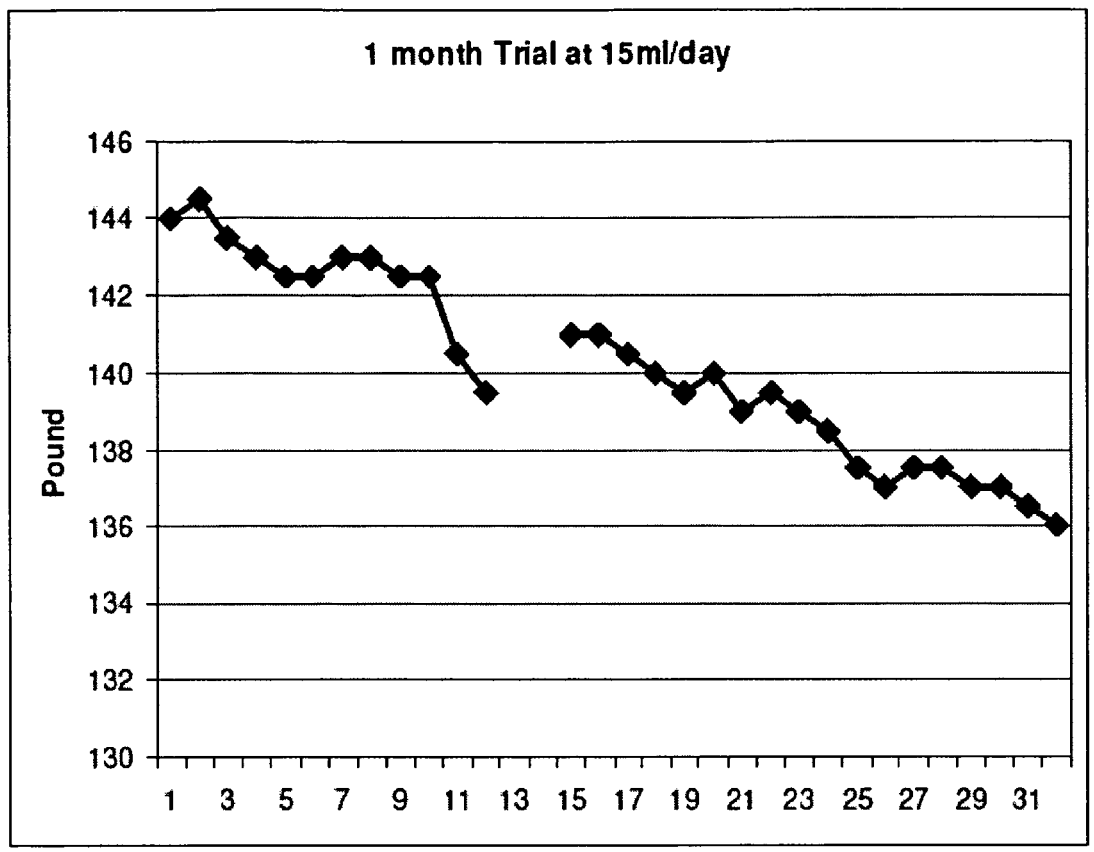
Figure 12:
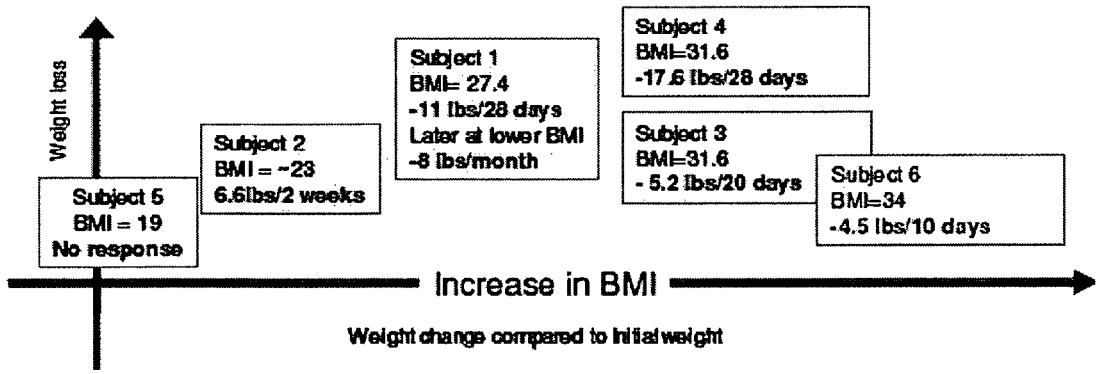
Figure 13A:
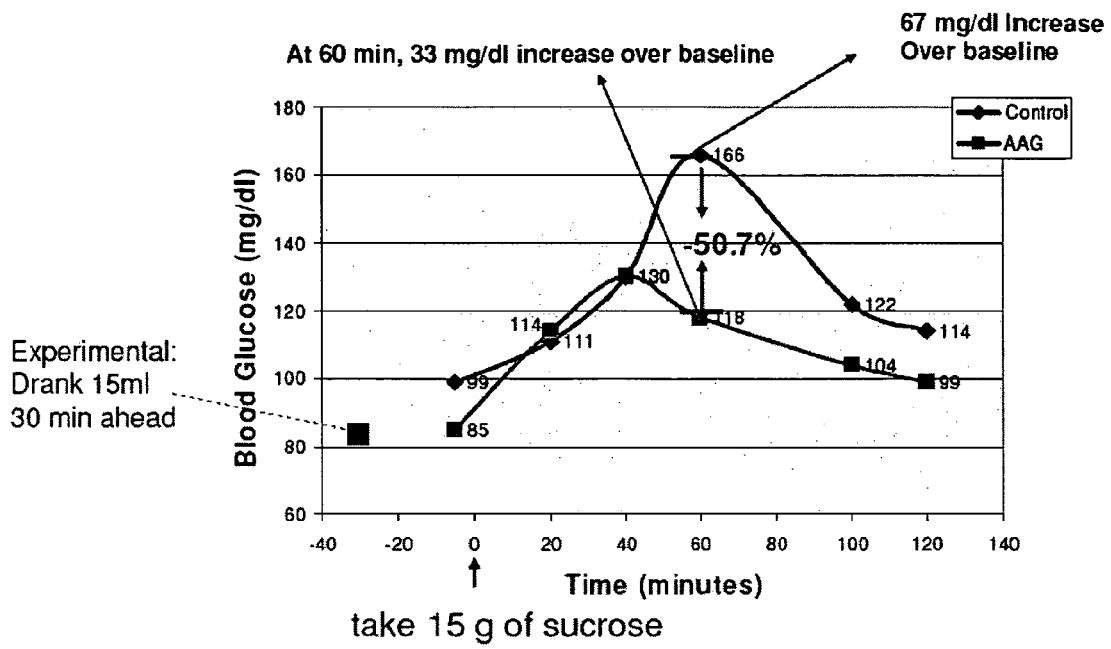
Figure 13:
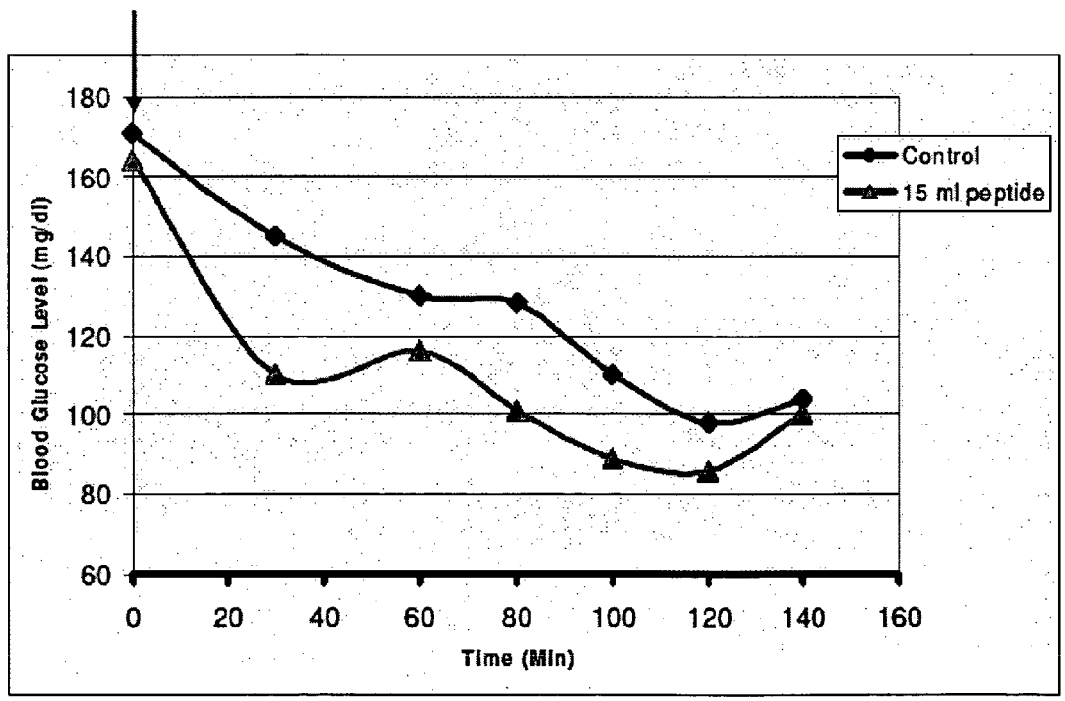
Figure 13:
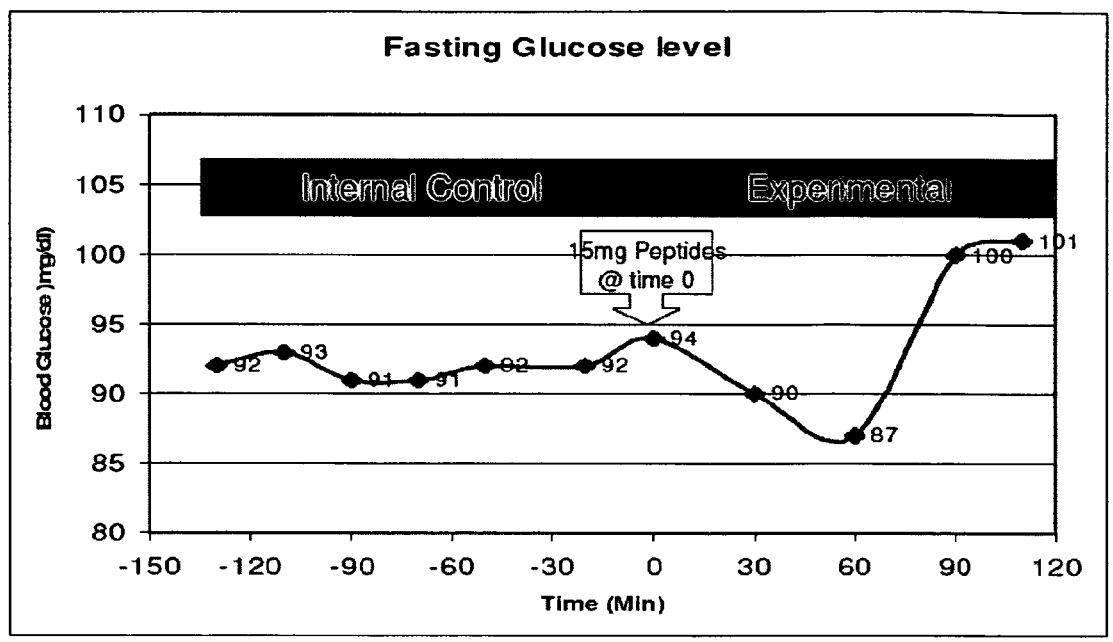

FIG. 1 provides leveling off of weight gain in the mice upon administration of a composition of the invention;

FIG. 2 provides weight loss of a human subject given a composition of the invention twice a day (3 mg/kg body weight) for ten days;

FIGS. 3A-B provide inhibition of mouse (FIG. 3A) and rat (FIG. 3B) insulin receptor activity by a composition of the invention;

FIG. 4A provides adipocytes treated with a composition of the invention at 20 μg/ml;

FIG. 4B provides adipocytes treated with a composition of the invention at 2 μg/ml;

FIG. 5 provides reduced weight gain in obese mice treated with a composition of the invention versus control;

FIG. 6 provides reduced weight gain in obese mice while treated with a composition of the invention and for a few days following treatment;

FIG. 7 provides reduction in weight of rats treated orally with a composition of the invention;

FIG. 8 provides reduction in oil droplets in the livers (fatty liver) of rats treated with a composition of the invention;

FIG. 9 provides weight loss in a human over a 60 day trial;

FIG. 10 provides weight loss in a human as a function of dose;

FIG. 11 provides weight loss in a human over one month;

FIG. 12 provides weight loss in six human subjects;

FIGS. 13A-C provide reduction in blood glucose in human subjects administered a composition of the invention.

5. DETAILED DESCRIPTION OF THE INVENTION

This patent application describes the novel compositions and methods of preparation thereof as well as methods for the treatment or prevention of obesity and overweight. Specifically, the compositions comprise zinc-charged proteins and proteolytic fragments thereof derived from, for example, serum or milk.

5.1 Definitions

As used herein, and unless otherwise indicated, the term "protein" refers to a molecule comprising one or more polypeptide chains, or a fragment thereof. Since the polypeptide chain can be modified with, for example, one or more saccharides or oligosaccharides, the term protein specifically includes glycoproteins. The term protein, unless indicated otherwise, has no size limitation. In particular, the term includes protease digested fragments of proteins, including glycoproteins, from, for example, serum or milk. Preferred proteases for digestion include papain.

As used herein and unless otherwise indicated, the terms "treat," "treating" and "treatment" refer to alleviating or reducing the severity of a symptom associated with the disease or condition being treated. For example, the terms "treating obesity" and "treatment of overweight" refer to relief from one or more symptoms associated with obesity or overweight.

As used herein and unless otherwise indicated, the terms "manage," "managing" and "management" refer to maintaining a reduction in severity or avoidance of a symptom associated with the disease or condition being managed.

As used herein and unless otherwise indicated, the terms "prevent," "preventing" or "prevention" refers to reducing risk of or delaying the onset of acquiring a disease or condition being prevented, or a symptom thereof. For example, the terms "preventing obesity" and "prevention of overweight" refer to reducing risk of or delaying the onset of one or more symptoms associated with obesity or overweight.

As used herein "subject" is an animal, typically a mammal. In preferred embodiments, the subject is a human, such as a patient.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of two therapeutic agents either simultaneously, concurrently or sequentially with no specific time limits. In one embodiment, both agents are present in a subject at the same time or exert their biological or therapeutic effect at the same time. In one embodiment, the two therapeutic agents are in the same composition or unit dosage form. In another embodiment, the two therapeutic agents are in separate compositions or unit dosage forms.

The term "dietary supplement" refers to materials defined as dietary supplements in Section 3 of the Dietary Supplement Health and Education Act of 1994, Public Law 103-417, Oct. 25, 1994. A dietary supplement is a product taken by mouth that contains a "dietary ingredient" intended to supplement the diet. The "dietary ingredients" include the zinc-charged, protease digested compositions of the invention and optionally one or more other dietary ingredients such as vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders.

5.2 Embodiments of the Invention

The present invention is directed to compositions and methods for treating or preventing obesity or overweight. In certain embodiments, the compositions and methods can reduces the number of fat cells of a subject through apoptosis. The methods can differ from the conventional methods of weight reduction, including suppressing appetite, limiting food intake or removing fat cells from a single area of the body.

Apoptosis is an active process of gene-directed cellular self-destruction, also called "programmed cell death." This process is marked by cell shrinkage, membrane changes and DNA fragmentation. Programmed cell death is thus different from the death caused by cell injury, which is called necrosis.

It has been previously shown that fetal serum contains protease sensitive apoptosis-inducing activity towards various cancer cell lines as well as tumors in experimental animals. At the same time, a zinc-binding protein, called fetuin or α-2-HS-glycoprotein (AHSG) was isolated from serum. Purified fetuin is capable of inducing apoptosis in cancer cells. This apoptotic activity is greatly enhanced by supercharging fetuin with zinc. In addition, a mixture of peptide fragments resulting from the digestion of zinc-charged fetuin also has been shown to induce apoptosis in cancer cells. (Yu, C. L. and Tsai, M. H., (2001) *Cancer Letters* 166:173-184; Yu, C. L. and Tsai, M. H., (2001) *Anticancer Research* 21:1839-1856).

In addition to fetuin, fetal and adult animal (cow, sheep, mouse and rat) and human sera contain other zinc-binding proteins, including α-1-acid glycoprotein (AAG), α-1-antitrypsin (AAT). It is now disclosed that these proteins (fetuin, AAG, and AAT), when charged with zinc, have apoptosis-inducing activity towards the 3T3-L1 mouse adipocyte cell line. In addition, the fragments obtained through protease digestion of these proteins also induce apoptosis in the 3T3-L1 adipocyte cell line. On the contrary, if not charged with zinc, neither the proteins nor the fragments induce apoptosis under the same conditions. While not intending to be bound by any particular theory of operation, it is believed that zinc-charging is, in part, a basis for the therapeutic activity of the compositions of the methods. The zinc-charging, as described in the sections below, yields compositions with substantially different bound zinc than, for example, native serum or milk proteins.

It is now further disclosed that, in addition to serum, anti-obesity protein fragments can be derived from milk. When whole milk was treated with zinc and protease to yield zinc-charged, protease digested milk proteins. The resulting zinc-charged, protease digested milk proteins also induced apoptosis in the 3T3-L1 cell line.

To test the in vivo anti-obesity properties, the fragments resulting from the protease digestion of AAG charged with zinc were intravenously administered to experimental animals. Despite being fed a special high fat diet, the animals did not gain weight and suffered no adverse side effects. To further test the weight loss properties, the AAG fragments were orally given to a human subject twice a day. After ten days, the body weight of the human subject decreased by 4.4 pounds.

5.3 Compositions and Preparation Thereof

Provided herein are compositions that can be used to treat or prevent obesity or overweight in a subject in need thereof.

In certain embodiments, a composition of the invention comprises a zinc-charged, protease digested serum or milk protein in an effective amount for use in a method of the invention. In certain embodiments, the amount is effective to treat obesity. In certain embodiments, the amount is effective to treat overweight. In certain embodiments, the amount is effective to prevent obesity. In certain embodiments, the amount is effective to prevent overweight. In certain embodiments, the amount is effective to reduce weight gain in the subject. In certain embodiments, the amount is effective to induce weight loss in the subject. In certain embodiments, the amount is effective to induce apoptosis of an adipocyte. In certain embodiments, the amount is effective to modulate insulin receptor activity.

The protein can be from any source apparent to those of skill in the art. In certain embodiments, the protein is isolated from blood serum. In certain embodiments, the protein is isolated from milk. The serum or milk can be from an animal such as a cow, sheep, mouse, rat or human. The blood serum can be adult or fetal blood serum. The milk or serum can be obtained and/or prepared according to any technique apparent to those of skill in the art.

In certain embodiments, the protein can be produced and isolated from recombinant sources according to techniques known to those of skill in the art. In certain embodiments, the protein can be produced by synthetic or semi-synthetic techniques known to those of skill in the art. In further embodiments, the protein can be obtained from a commercial source.

The milk or serum protein can be any milk or serum protein effective for the methods provided herein. In certain embodiments, the serum or milk protein is selected from the group consisting of α-2-HS-glycoprotein, α-1-acid glycoprotein, α-1-antitrypsin, albumin and transferrin. In certain embodiments, the serum or milk protein is α-2-HS-glycoprotein. In certain embodiments, the serum or milk protein is α-1-acid glycoprotein. In certain embodiments, the serum or milk protein is α-1-antitrypsin. In certain embodiments, the serum or milk protein is albumin. In certain embodiments, the serum or milk protein is transferrin.

In certain embodiments, the composition comprises more than one serum or milk protein is selected from the group consisting of α-2-HS-glycoprotein, α-1-acid glycoprotein, α-1-antitrypsin, albumin, transferrin and α-fetoprotein. In certain embodiments, the composition comprises two serum or milk proteins selected from the group consisting of α-2-HS-glycoprotein, α-1-acid glycoprotein, α-1-antitrypsin, albumin, transferrin and α-fetoprotein. In certain embodiments, the composition comprises three serum or milk proteins selected from the group consisting of α-2-HS-glycoprotein, α-1-acid glycoprotein, α-1-antitrypsin, albumin, transferrin and α-fetoprotein. In certain embodiments, the composition comprises four serum or milk proteins selected from the group consisting of α-2-HS-glycoprotein, α-1-acid glycoprotein, α-1-antitrypsin, albumin, transferrin and α-fetoprotein. In certain embodiments, the composition comprises five serum or milk proteins selected from the group consisting of α-2-HS-glycoprotein, α-1-acid glycoprotein, α-1-antitrypsin, albumin, transferrin and α-fetoprotein.

In the compositions of the invention, the serum or milk protein is zinc-charged. As discussed below, zinc-charging yields a composition with bound zinc that is substantially different from the trace amount of zinc that might be present in native serum or milk. The serum or milk protein can be zinc-charged according to any technique apparent to those of skill in the art. Exemplary techniques are described, for example, in U.S. Pat. Nos. 5,994,298, 6,258,779, 6,720,311 and 6,737,402, the contents of which are hereby incorporated by reference in their entireties. Proteins can be zinc-charged by removing bound ions, such as metal ions, followed by contacting the proteins with zinc ion. Bound ions can be removed by any technique apparent to those of skill in the art including, for example, dialysis, filtration, chelating agents, etc. In certain embodiments, bound ions are removed by contacting the proteins with an effective amount of a chelating agent such as EDTA or EGTA. Exemplary conditions include, for example, about 5 mM to about 100 mM EDTA for about 40 μM protein. In certain embodiments, following removal of bound ions the chelating agent is removed from the proteins by a standard technique such as filtration, dialysis, chromatography or molecular sieves.

The proteins can be charged with zinc by contact with zinc in any form in an amount effective to charge the proteins with zinc. Exemplary forms of zinc include zinc salts such as zinc chloride, zinc acetate and zinc sulfate. In the working examples below, the proteins are charged with zinc acetate. Exemplary conditions include, for example, about 50 to about 500 mM zinc salt, e.g. zinc acetate, zinc chloride or zinc sulfate, for 40 μM protein. Particular conditions include about 50 to about 500 mM zinc acetate for 40 μM protein. In certain embodiments, excess zinc is removed from the proteins by standard techniques such as filtration, dialysis, chromatography or molecular sieves.

In the compositions of the invention, the proteins are protease digested. The proteins can be protease digested prior to zinc-charging, during zinc-charging or following zinc charging. In the working examples below, zinc-charging is followed by protease digestion. The protease can be any protease known to those of skill in the art that is capable of generating fragments effective in the methods of the invention. Exemplary proteases include papain. The proteins are contacted with the protease under conditions suitable for generating fragments effective in the methods of the invention. In certain embodiments, the proteins are contacted with papain at 37° C. for about two hours or more. In certain embodiments, papain is removed from the proteins by standard techniques such as filtration, dialysis, chromatography or molecular sieves. In certain embodiments, the proteins can be digested by other techniques known to those of skill in the art, such as a freeze-thaw technique.

In certain embodiments, the zinc-charged, protease digested serum or milk protein as described herein is substantially of a size less than 100 kDa, 50 kDa, 25 kDa, 20 kDa, 15 kDa, 10 kDa, 5 kDa or 3 kDa. The term "substantially of a size less than" indicates no more than 50%, 75%, 90% or 95% of the protease digested serum or milk protein fragments are greater than the size limit. The zinc-charged, protease digested serum or milk protein fragments can be sized according to any technique apparent to those of skill in the art including, for example, filtration, dialysis, chromatography or molecular sieves.

The compositions can be formulated into a form described in the sections below, such as a dietary supplement, a food additive, a food composition, a nutraceutical composition or a pharmaceutical composition, by standard techniques, including those described below.

5.4 Methods of Use

Provided herein are methods of treating or preventing obesity or overweight with one or more compositions of the invention.

In certain embodiments, provided herein are methods of treating obesity with one or more of the compositions of the invention. Such methods comprise the step of administering to a subject in need thereof an effective amount of a composition of the invention to treat obesity. In certain embodiments, provided herein are methods of preventing obesity with one or more of the compositions of the invention. Such methods comprise the step of administering to a subject in need thereof an effective amount of a composition of the invention to prevent obesity.

In certain embodiments, provided herein are methods of treating overweight with one or more of the compositions of the invention. Such methods comprise the step of administering to a subject in need thereof an effective amount of a composition of the invention to treat overweight. In certain embodiments, provided herein are methods of preventing overweight with one or more of the compositions of the invention. Such methods comprise the step of administering to a subject in need thereof an effective amount of a composition of the invention to prevent overweight.

In certain embodiments, provided herein are methods of reducing weight gain with one or more of the compositions of the invention. Such methods comprise the step of administering to a subject in need thereof an effective amount of a composition of the invention to reduce weight gain. In certain embodiments, provided herein are methods of preventing weight gain with one or more of the compositions of the invention. Such methods comprise the step of administering to a subject in need thereof an effective amount of a composition of the invention to prevent weight gain.

In certain embodiments, provided herein are methods of inducing weight loss with one or more of the compositions of the invention. Such methods comprise the step of administering to a subject in need thereof an effective amount of a composition of the invention to induce weight loss. In certain embodiments, the weight loss is for medical reasons. In certain embodiments, the weight loss is cosmetic weight loss.

In certain embodiments, provided herein are methods of treating or preventing diseases or disorders related to overweight or obesity. Such diseases or disorders include, for example, high blood pressure, hypertension, high blood cholesterol levels, diabetes, insulin resistance, glucose intolerance, coronary heart disease and psychological disorders, such as depression and eating disorders. Such methods comprise the step of administering to a subject in need thereof an effective amount of a composition of the invention to treat or prevent the disease or disorder.

In certain embodiments, provided herein are methods of inducing apoptosis in an adipocyte with one or more of the compositions of the invention. Such methods comprise the step of contacting the adipocyte with an effective amount of a composition of the invention to induce apoptosis. The adipocyte can be any adipocyte known to those of skill in the art including an adipocyte in vivo, in vitro or ex vivo. In certain embodiments, the adipocyte can be in a subject.

In certain embodiments, provided herein are methods of modulating epidermal growth factor receptor (EGFR) function in a cell with one or more of the compositions of the invention. Such methods comprise the step of contacting cell expressing EGFR with an effective amount of a composition of the invention to modulate receptor activity. The cell expressing EGFR can be any cell expressing any EGFR known to those of skill in the art including cell expressing EGFR in vivo, in vitro or ex vivo. In certain embodiments, the cell expressing EGFR can be in a subject.

In certain embodiments, provided herein are methods of modulating insulin receptor function in a cell with one or more of the compositions of the invention. Such methods comprise the step of contacting cell expressing the insulin receptor with an effective amount of a composition of the invention to modulate receptor activity. The cell expressing the insulin receptor can be any cell expressing any insulin receptor known to those of skill in the art including cell expressing the insulin receptor in vivo, in vitro or ex vivo. In certain embodiments, the cell expressing the insulin receptor can be in a subject.

5.4.1 Subject Populations

The subject can be any subject in need of a method of the invention. In certain embodiments, the subject is an animal. In certain embodiments, the subject is a human. In certain embodiments, the subject is a patient.

In certain embodiments, the subject is a human at risk for obesity. In certain embodiments, the subject is an obese human. As used herein, "obese" refers to a subject considered obese by practitioners of skill in the art. In certain embodiments, "obese" refers to a human with a body mass index (BMI) of 30 kg/m$^2$ or greater.

In certain embodiments, the subject is a human at risk for overweight. In certain embodiments, the subject is an overweight human. As used herein, "overweight" refers to a subject considered overweight by practitioners of skill in the art. In certain embodiments, "overweight" refers to a human with a body mass index (BMI) of 25 kg/m$^2$ or greater.

In certain embodiments, the subject is a human with a BMI of greater than 30 kg/m$^2$, 35 kg/m$^2$, 40 kg/m$^2$, 45 kg/m$^2$ or 50 kg/m$^2$. In certain embodiments, the subject is a human with a BMI of less than 25 kg/m$^2$ for instance a human with a BMI of less than 25 kg/m$^2$ that needs to reduce weight or weight gain according to a practitioner of skill in the art.

In certain embodiments, the subject is healthy. In certain embodiments, the subject is healthy other than overweight or obesity. In certain embodiments, the subject is not healthy. In certain embodiments, the subject is not healthy in addition to being overweight or obese.

In certain embodiments, the subject is healthy or not healthy, and a composition of the invention is administered to reduce weight gain or induce weight loss for any reason at all.

5.4.2 Combinations

In another aspect, the present invention provides methods of administering to an individual in need thereof a composition of the invention in combination with a second agent effective to treat or prevent obesity, to treat or prevent overweight, to effect weight loss or to reduce weight gain.

In certain embodiments, the second agent modulates α-melanocyte stimulating hormone (α-MSH). In some embodiments, the second agent is selected from the group consisting of a selective serotonin reuptake inhibitor (SSRI), a serotonin 2C agonist, and a serotonin 1B agonist. In further embodiments, the second agent is selected, e.g., from the group consisting of bupropion, fluoxetine, fluvoxamine, sertraline, paroxetine, citalopram, escitalopram, sibutramine, duloxetine, and venlafaxine, and a pharmaceutically acceptable salt or prodrug thereof. In other embodiments, the second agent suppresses the activity of neuropeptide Y. In further embodiments, the second agent is selected from the group consisting of NPY antagonists, ghrelin antagonists, and leptin. In certain other embodiments, the second agent agonizes NPY Y2 receptor. In some embodiments, the second agent is an NPY receptor antagonist. Other embodiments of the present invention include those in which the second agent is selected from the group consisting of a γ-amino butyric acid (GABA) inhibitor, a GABA receptor antagonist, and a GABA channel antagonist. The GABA inhibitor may be a 5-HT1b agonist or another agent that inhibits the activity of GABA neurons. In other embodiments the second agent is a dopamine reuptake inhibitor. Phentermine is an example of a dopamine reuptake inhibitor. In certain other embodiments, the second agent is a norepinephrine reuptake inhibitor. Examples of norepinephrine reuptake inhibitors include thionisoxetine, and reboxetine. Other embodiments include those in which the second agent is a dopamine agonist. Some dopamine agonists that are available on the market include cabergoline, amantadine, lisuride, pergolide, ropinirole, pramipexole, and bromocriptine. In further embodiments, the second agent is a norepinephrine releaser, for example diethylpropion, or a mixed dopamine/norepinephrine reuptake inhibitor, for example, atomoxatine. In certain other embodiments, the second agent is a 5-HT1b agonist, such as sumatriptan, almotriptan, naratriptan, frovatriptan, rizatriptan, zomitriptan, and elitriptan. In further embodiments, the second agent is an anticonvulsant. The anticonvulsant may be selected from the group consisting of zonisamide, topiramate, nembutal, lorazepam, clonazepam, clorazepate, tiagabine, gabapentin, fosphenyloin, phenyloin, carbamazepine, valproate, felbamate, levetiracetam, oxcarbazepine, lamotrigine, methsuximide, and ethosuxmide. In some embodiments, the second agent is a cannabinoid receptor antagonist.

In certain embodiments, the second agent itself may be a combination of two or more agents. For example, the second agent may be a combination of a dopamine reuptake inhibitor and a norepinephrine reuptake inhibitor, e.g. mazindol. Alternatively, the second agent may be a combination of a SSRI and a norepinephrine reuptake inhibitor, such as sibutramine, venlafaxine, and duloxetine.

5.5 Dietary Supplements and Pharmaceutical Compositions

The composition of the invention can be useful in the form of a food, a food additive, a dietary supplement, a nutraceutical or a pharmaceutical. The compositions may contain a carrier, a diluent, or an excipient. Depending on the intended use, the carrier, diluent, or excipient may be chosen to be suitable for human or veterinary use, food, additive, supplement or pharmaceutical use.

In certain embodiments, a composition of the invention is provided in a mixture with milk. In certain embodiments, a composition of the invention is provided in the form of a dried powder. The composition of the invention can be dried according to any technique known to those of skill in the art including lyophilization, freeze drying, spray drying and evaporative drying. The powder can comprise a composition of the invention and optionally any carrier, diluent, excipient or other additive described herein or known to those of skill in the art. In certain embodiments, a composition of the invention is provided in the form of a liquid. The liquid can comprise a composition of the invention and optionally any carrier, diluent, excipient or other additive described herein or known to those of skill in the art. The liquid can be any volume deemed useful by one of skill in the art, for instance, a volume convenient for the dosage and route of administration.

As used herein a "food" or "food composition" is a material consisting essentially of protein, carbohydrate and/or fat, which is used in the body of an organism to sustain growth, repair and vital processes and to furnish energy. Foods may also contain supplementary substances such as minerals, vitamins and condiments. The term food includes a beverage adapted for human or animal consumption. As used herein a "food additive" is as defined by the FDA in 21 CFR 170.3(e)(1) and includes direct and indirect additives.

Compositions provided herein can be formulated using standard formulation techniques into gel caps, teas, tablets, etc. See, e.g., Remington's Pharmaceutical Sciences, 18th ed., Mack Publishing, Easton Pa. (1990). Compositions of the invention may be formulated into a dietary supplement or a pharmaceutical preparation for the administration to subject for the treatment or prevention of obesity or overweight as described herein.

Suitable forms of compositions of the invention include food additives, food compositions (including beverage compositions) and dietary supplements. The compositions of the invention may be added to various foods so as to be consumed simultaneously. As a food additive, the compositions of the invention may be used in the same manner as conventional food additives, and thus, only need to be mixed with other food components.

It will be recognized that dietary supplements may not necessarily use the same formulation ingredients or have the same sterile and other FDA requirements as pharmaceutical compositions. The dietary supplements may be in liquid form, for example, solutions, syrups or suspensions, or may be in the form of a product for reconstitution with water or any other suitable liquid before use. Such liquid preparations may be prepared by conventional means such as a tea, health beverage, dietary shake, liquid concentrate, or liquid soluble tablet, capsule, pill, or powder such that the beverage may be prepared by dissolving the liquid soluble tablet, capsule, pill, or powder within a liquid and consuming the resulting beverage. Alternatively, the dietary supplements may take the form of tablets or capsules prepared by conventional means and optionally including other dietary supplements including vitamins, minerals, other herbal supplements, binding agents, fillers, lubricants, disintegrants, or wetting agents, as those discussed above. The tablets may be coated by methods well-known in the art. In a preferred embodiment, the dietary supplement may take the form of a capsule or powder to be dissolved in a liquid for oral consumption.

The magnitude of the dietary dose of an active ingredient in the treatment or prevention of a disease or condition will vary with the severity of the disease or condition to be treated and the route of administration. The dose, and perhaps the dose frequency, will also vary according to age, body weight, response, and the past medical history of the consumer or patient. Suitable dosing regimens can be readily selected by those skilled in the art with due consideration of such factors.

The amount of composition of the invention incorporated into a food product will depend on the kind of food and the desired effect. In general, a single serving comprises an amount of the composition of the invention that is about 0.1% to about 100% or 0.1% to about 50% or about 0.5% to about 20% of the food composition. In certain embodiments, a food product comprises the composition of the invention extract in an amount of about 1% to about 10% by weight of the food composition.

Examples of food include, but are not limited to, confectionery such as sweets (candies, jellies, jams, etc.), gums, bean pastes, baked confectioneries or molded confectioneries (cookies, biscuits, etc.), steamed confectioneries, cacao or cacao products (chocolates and cocoa), frozen confectioneries (ice cream, ices, etc.), beverages (fruit juice, soft drinks, carbonated beverages), health drinks, health bars, and tea (green tea, black tea, etc.).

Further within the scope of the invention is a package comprising a food, a dietary supplement or a pharmaceutical, and a label indicating the presence of a composition of the invention. Optionally, the label may indicate the composition of the invention, the beneficial properties of the composition of the invention and instructions for use. A In a preferred embodiment, a composition for administration is a pharmaceutical composition or a single unit dosage form. Pharmaceutical compositions and single unit dosage forms can comprise a prophylactically or therapeutically effective amount of one or more prophylactic or therapeutic agents, and a typically one or more pharmaceutically acceptable carriers or excipients or diluents. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin. Nutraceutical compositions can, but need not, comprise one or more active or inactive ingredients that are not necessarily considered pharmaceutically acceptable to current practitioners in the art.

A pharmaceutical or nutraceutical composition of the invention can be administered by any route according to the judgment of those of skill in the art, including but not limited to orally, intravenously, intragastrically, intraduodenally, intraperitoneally or intracerebroventricularly.

Typical pharmaceutical or nutraceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical or nutraceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose-free compositions of the invention can comprise excipients that are well known in the art and are listed, for example, in the U.S. Pharmocopia (USP)SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre-gelatinized starch, and magnesium stearate.

The invention further encompasses administration of pharmaceutical or nutraceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical or nutraceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the patient. The formulation should suit the mode of administration. In a preferred embodiment, the pharmaceutical compositions or single unit dosage forms are sterile and in suitable form for administration to a subject, preferably an animal subject, more preferably a mammalian subject, and most preferably a human subject.

A pharmaceutical or nutraceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical or nutraceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the composition will typically vary depending on their use. For example, a dosage form used in the acute treatment of a disorder may contain larger amounts of one or more of the composition it comprises than a dosage form used in the chronic treatment of the same disease. Also, the therapeutically effective dosage form may vary among different types of diseases or disorders. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions comprising the composition are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms for administration in methods of the invention comprise a composition of the invention in an amount within the range of from about 0.1 mg to about 400 mg per day, 1 mg to 100 mg per day, or 1 mg to 15 mg per day given as a single once-a-day dose or as divided doses throughout the day. Particular dosage forms of the invention have about 0.1, 0.2, 0.25, 0.3, 0.5, 0.75, 1.0, 2.0, 2.5, 3.0, 5.0, 7.5, 10.0, 15.0, 20.0, 25.0, 40.0, 50.0, 60.0 or 100 mg of the composition. Exemplary dosage forms are 3, 5, 7.5 or 15 ml of a liquid composition having a protein concentration of 0.1 mg/ml.

Pharmaceutical compositions used in the methods of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In certain embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

5.6 Dosage & Frequency of Administration

The amount of the composition in the methods of the invention which will be effective in the prevention, treatment, management, or amelioration of a disorder or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems.

Exemplary doses of a composition of the invention include milligram or microgram amounts of total proteins per kilogram of subject or sample weight (e.g., about 1 microgram per kilogram to about 10 milligrams per kilogram). For a composition used in the invention, the dosage administered to a patient can be between 0.001 mg/kg to about 100 mg/kg. In certain embodiments, the dosage administered to a patient is between 0.001 mg/kg and about 10 mg/kg. In certain embodiments, the dosage is from about 0.02 mg/kg to about 4.0 mg/kg of the patient's body weight, based on weight of the proteins in the composition. In embodiments where pure protein (e.g. recombinant protein or commercially available protein) is the starting material, the dosage can be at the lower end of the range. In embodiments where protein is prepared from milk or serum, the dosage can be at the high end of the range.

In general, the recommended daily dose range of a composition in the methods of the invention for the conditions described herein lie within the range of from about 0.1 mg to about 100 mg per day, as a single dose or multiple doses per day. The actual dosage can be determined by a practitioner of skill in the art according to, for example, the subjects age, body weight, BMI or other factors. In certain embodiments, a total daily dose range can be from about 0.1 mg to about 25 mg per day, more specifically or between about 1 mg to about 15 mg per day.

The composition can be administered as a single once-a-day dose or as divided doses throughout a day. In some embodiments, the daily dose is administered twice daily in equally divided doses. In other embodiments, the daily dose is administered three times per day. In particular embodiments, the daily dose is administered three times per day in equally divided doses. In particular embodiments, the daily dose is administered four times per day in equally divided doses.

As described herein, weights are preferably based on weight of zinc-charged, protease digested protein.

In certain embodiments, administration of a composition in the invention may be repeated daily. In certain embodiments and the administrations may be separated by at least 1 day, 2 days or 3 days.

An effective amount of a composition described herein will provide therapeutic benefit without causing substantial toxicity.

Toxicity of a composition can be determined by standard pharmaceutical procedures in cell cultures or experimental animals, for example, by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1996, In: The Pharmacological Basis of Therapeutics, $9^{th}$ ed., Chapter 2, p. 29, Elliot M. Ross).

6. EXAMPLES

6.1 Example 1

Preparation of Zinc-Charged Proteins

Method 1: Forty milliliters of serum (from various animals) is incubated with 8 ml of 0.1M EDTA or EGTA (dissolved in water) for 1 hour. EDTA or EGTA is removed by dialysis against 4 liters of de-ionized water for 3 hours. The EDTA or EGTA-treated serum is incubated with zinc acetate (at final Zn concentration of 50 mM) for at least 4 hours. The precipitates are removed by centrifugation. The 40 ml of serum are subjected to two rounds of dialysis against de-ionized water to remove excess zinc: first, against 10 liters for 18 hours and then, against fresh 4 liters for another 4 hours.

Method 2: Forty milliliters of milk (from various animals) is incubated with 8 ml of 0.1M EDTA or EGTA (dissolved in water) for 1 hour. EDTA or EGTA is removed by dialysis against 4 liters of de-ionized water for 3 hours. The EDTA-treated milk is incubated with zinc acetate (at final Zn concentration of 50 mM) for at least 4 hours. The precipitates are removed by centrifugation. The 40 ml of milk are subjected to two rounds of dialysis against de-ionized water to remove excess zinc: first, against 10 liters for 18 hours and then, against fresh 4 liters for 4 another hours.

Method 3: A protein solution (40 μM each of α-2-HS-glycoprotein (AHSG, or fetuin), α-1-acid glycoprotein (AAG), α-1-antitrypsin (AAT), albumin, transferrin and α-fetoprotein) is incubated with 25 mM EDTA or EGTA in a 10 ml saline solution containing 2 mM HEPES, pH 7.0, for 1 hour at room temperature. EDTA or EGTA is removed by repetitive filtration through a molecular sieve with a molecular weight cut-off of 10 KDa. The protein solution (40 μM) is incubated with 250 mM zinc acetate for 18 hours. The excess zinc ions are removed by four rounds of concentration against 20 volumes of saline solution (pH 7.0), each time using a molecule sieve, which resulted in a dilution factor of $6 \times 10^{-6}$ of zinc ions. The free zinc ion concentration is determined from the 10 KDa membrane filtrate of the protein solution to be about 5-10 μM, a concentration at which no cytotoxicity has been previously observed.

Method 4: A protein solution (40 μM each of α-2-HS-glycoprotein (AHSG, or fetuin), α-1-acid glycoprotein (AAG), α-1-antitrypsin (AAT), albumin, transferrin and α-fetoprotein) is incubated with 5 mM EDTA or EGTA in a 10 ml saline solution containing 2 mM HEPES, pH 7.0, for 1 hour at room temperature. EDTA or EGTA is removed by repetitive filtration through a molecular sieve with a molecular weight cut-off of 10 KDa. The protein solution (40 μM) is incubated with 80 μM of zinc acetate for 18 hours.

Method 5: A protein solution (40 μM each of α-2-HS-glycoprotein (AHSG, or fetuin), α-1-acid glycoprotein (AAG), α-1-antitrypsin (AAT), albumin, transferrin and α-fetoprotein) is incubated with 25 mM EDTA or EGTA in a 10 ml saline solution containing 2 mM HEPES, pH 7.0, for 1 hour at room temperature. EDTA or EGTA is removed by repetitive filtration through a molecular sieve with a molecular weight cut-off of 10 KDa. The protein solution (40 μM) is incubated with 50 mM zinc acetate for 18 hours. The excess zinc ions are removed by dialysis against 1000 volumes of de-ionized water for 2 hours.

6.2 Example 2

Digestion of Zinc-Charged Proteins with Protease

Method 1: Zinc-charged serum prepared as described above (40 ml) is incubated with papain (2,500 units, from papaya latex) for 2 hours at 37° C. The fragments are collected by passing the incubation mixture through a molecular sieve with a molecular weight cut-off at 3 KDa and up to 10 KDa.

Method 2: Zinc-charged milk prepared as described above (40 ml) is incubated with papain (2,500 units, from papaya latex) for 2 hours at 37° C. The fragments are collected by passing the incubation mixture through a molecular sieve with a molecular weight cut-off at 3 KDa and up to 10 KDa.

Method 3: Zinc-charged proteins prepared as described above (5 ml containing 40 μM each of α-2-HS-glycoprotein (AHSG, or fetuin), α-1-acid glycoprotein (AAG), α-1-antit-rypsin (AAT), albumin, transferrin and α-fetoprotein) are incubated with papain (468 units, from papaya latex) for 2 hours at 37° C. The fragments are collected by passing the incubation mixture through a molecular sieve with a molecular weight cut-off at 3 KDa.

6.3 Example 3

Animal Study

Three A/J mice (6 weeks old, 18-20 grams) kept on a high fat diet and water ad libitum were kept in a cage. After 4 days, the mice were intravenously tail-injected with fragments of AAG prepared in accordance with the above method in the amount 2 mg/Kg body weight for 6 days. The body weights were measured daily.

Fragments of AAG Inhibit Weight Gain in Mice

As shown in FIG. 1, the injection of the AAG fragments prepared according to methods described above causes the leveling off of weight gain in the mice (day 5-11). The body weight of the mice remained constant for 6 days after the termination of the injection of the fragments (day 12-17).

6.4 Example 4

Human Trial

Compositions from serum prepared in accordance with the above method were orally given to a human subject kept on a normal diet twice a day for ten days. The dosage given was 0.02 mg/kg body weight, but the effective range can be, for example, between 0.02 mg/kg body weight and 4 mg/kg body weight. The body weight was measured daily.

Protein Fragments from Serum Cause Weight Loss in Human

FIG. 2 shows the weight loss of a human subject given composition from serum prepared according to methods described above twice a day (3 mg/kg body weight) for ten days. It was found that the human subject kept on a normal diet lost 4.4 pounds after 10 days of treatment with the fragments.

6.5 Example 5

Compositions of the Invention Inhibit Mouse and Rat Insulin Receptor

A cell lysate from mouse adipocyte cell line 3T3-L1, and a rat insulin receptor (Sigma), were contacted with a composition of the invention prepared according to Example 2. As shown in FIG. 3, the composition of the invention inhibits insulin receptor signaling activity in the cell line as shown by a calorimetric ELISA assay for tyrosine kinase activity (K-LISA PTK Screening Kit, Calbiochem catalog no. 539701).

In FIG. 3A, wells 1 & 2 provide have basal tyrosine kinase activity for the 3T3-L1 cell lysate. Addition of the composition of the invention inhibits basal tyrosine kinase activity (wells 3 & 4; duplicates). When insulin is added to the adipocyte cell lysate, IR's tyrosine kinase activity is much stronger (wells 5 & 6). Addition of the composition of the invention abolished most of the insulin induced IR tyrosine kinase activity (wells 7 & 8).

In FIG. 3B, wells 1 & 2 provide have basal tyrosine kinase activity for the rat liver insulin receptor. Addition of the composition of the invention inhibits basal tyrosine kinase activity (wells 3 & 4; duplicates). When insulin is added, IR's tyrosine kinase activity is much stronger (wells 5 & 6). Addition of the composition of the invention abolished most of the insulin induced IR tyrosine kinase activity (wells 7 & 8).

6.6 Example 6

Compositions of the Invention Lower Insulin Levels in a Human

The instant example provides the effects of a composition of the invention on the blood chemistry of a human subject. The composition of the invention significantly lowered the subject's fasting insulin levels.

During the experimental phase, the human subject ingested a composition of the invention prepared according to Example 2 for one month. During the control phase, the human subject was monitored while ingesting no composition of the invention for one month.

Blood samples were taken at 3 different time points during the month. Each sample (in duplicate) was tested for fasting insulin and IGF-1 levels using ELISA assays.

The insulin level during the experimental phase was 1.38+/−0.04 µU/ml. The insulin level the control phase was 2.02+/−0.07 µU/ml. The composition of the invention lowered the subject's insulin level by 32%.

The IGF-1 level during the experimental phase was 96+/−7.8 ng/ml. The IGF-1 level the control phase was 98+/−2.4 ng/ml. The composition of the invention did not significantly alter IGF-1 levels.

Further, the subject's blood chemistry was measured during the experimental phase and the control phase. Notably, the composition of the invention significantly lowered the subject's uric acid (from 9.4 to 7.3), significantly lowered the subject's triglycerides (from 178 to 95) and slightly increased the subject's HDL (from 37 to 44).

6.7 Example 7

Compositions of the Invention Induce Apoptosis of Adipocytes

The instant example provides the effects of compositions of the invention on adipocytes. At lower doses, compositions of the invention inhibited oil drop formation in adipocytes. At higher doses, compositions of the invention induced apoptosis.

Pre-adipocytes were induced to differentiate into adipocytes. At a dose of 20 µg/ml, a composition of the invention according to Example 2 caused apoptosis in 6 to 8 hours (see FIG. 4A).

Pre-adipocytes were induced to differentiate into adipocytes. At a dose of 2 µg/ml, a composition of the invention according to Example 2 reduced or eliminated the formation of oil droplets in the adipocytes (FIG. 4B).

6.8 Example 8

Compositions of the Invention Reduce Weight Gain in Mice on a High Fat Diet The instant example provides the effects of compositions of the invention on mice fed a high fat diet. The composition of the invention significantly reduced weight gain over the trial period.

Mice (n=6) were fed a high fat diet prior to the trial to induce obesity. Control mice were treated with vehicle and a high fat diet. Experimental mice were treated with a composition of the invention by intraperitoneal injection (3 days) followed by intravenous injection (7 days).

Control mice gained twice as much body weight (average 16%) compared to experimental mice (average 7.69%). The intraperitoneal injection did not reduce weight gain in this trial, but the intravenous injection did significantly reduce weight gain (FIG. 5).

6.9 Example 9

Reduce Weight Gain in Mice on a High Fat Diet Depends on Dosing of Composition of the Invention The instant example provides the effects of compositions of the invention on mice fed a high fat diet. The same mice were treated with a composition of the invention and then removed from treatment to observe weight change with and without the treatment. The composition of the invention significantly reduced weight gain while administered and for two days following administration.

Mice were fed a high fat diet prior to the trial to induce obesity. Experimental mice were treated with a composition of the invention by intravenous injection (8 days) followed by control intravenous injection for the remaining days.

The mice did not gain weight while the composition was administered or during at least two following days. The mice returned to weight gain several days after treatment with the composition of the invention (FIG. 6).

6.10 Example 10

Oral Activity of a Composition of the Invention in Rats

The instant example provides oral activity of compositions of the invention in experimental rats.

Rats were treated (n=3) with a composition of the invention or a control (water; n=3) by oral gavage daily.

As shown in FIG. 7, treatment with a composition of the invention by oral administration significantly reduced body weight in the experimental rats.

6.11 Example 11

Reduction of Fatty Liver in Rats Treated with a Composition of the Invention in Rats In fatty liver, fat accumulates in the liver cells. Simple fatty liver usually does not damage the liver. A patient has fatty liver when the fat makes up at least 10% of the liver. It is most commonly associated with obesity, insulin resistance, and hyperlipidemia—all components of metabolic syndrome. Possible explanations for fatty liver include the transfer of fat from other parts of the body, or an increase in the extraction of fat presented to the liver from the intestine. Another explanation is that the fat accumulates because the liver is unable to change it into a form that can be eliminated. A study conducted in 2004 indicated that nearly ⅓ of American adults surveyed had fatty liver.

Rats were treated as described in Example 10. Liver samples were stained with Oil Red O, a stain for oil droplets. As shown in FIG. 8, treatment with a composition of the invention by oral administration significantly reduced oil deposits in the livers of treated rats.

6.12 Example 12

A Composition of the Invention Reduced Weight in a Human Over 60 Days

The instant example provides long term weight loss in a human over a period of 60 days.

The human subject ingested 5 mg of a composition of the invention orally three times per day over the 60 day period. As shown in FIG. 9, the subject steadily lost 16 pounds over the 60 days. The subject experienced no gross side effects.

6.13 Example 13

Effective Dosages of a Composition of the Invention in a Human Subject

The instant example provides the effect of reducing the dosage of the composition of the invention in the human subject of Example 12.

The human subject ingested 3 ml (0.1 mg/ml), 10 ml (0.1 mg/ml) and 15 ml (0.1 mg/ml) of the composition of the invention. Each dosage was administered over a separate 7 day period to the same human subject. As shown in FIG. 10, the 15 ml dosages led to substantial weight loss, but the 3 and 10 ml doses did not.

In this trial in this subject, the 15 ml dosage was more effective than the 3 ml or 10 ml dosages.

6.14 Example 14

Twice Daily Dosages of a Composition of the Invention Reduced Weight in a Human The instant example provides long term weight loss in a human when dosed twice per day in the human subject of Example 12.

The human subject ingested 7.5 ml (0.1 mg/ml) of a composition of the invention orally two times per day over a 32 day period. One dose was ingested in the morning and a second dose was ingested in the evening. As shown in FIG. 11, the subject steadily lost 8 pounds over the 32 days. The initial weight was 144 pounds and the final weight was 136 pounds.

In this subject under the trial conditions, a twice daily dose was as effective as a three times daily dose.

6.15 Example 15

Compositions of the Invention Reduced Weight in Humans

The instant example provides long term weight loss in a human over a total of four months as described in the previous examples. The doses, as described, were 3 mg/day, 10 mg/day or 15 mg/day. The doses were administered three times per day or two times per day as described above.

Over the entire four month period, the human subject (age 55) lost 29 pounds. His final body fat was 16% (22.4 pounds) and his final lean body mass was 83.6% (114.6 pounds). Blood chemistry showed reduced uric acid (9.4 to 7.3), total cholesterol (256 to 225) and triglycerides (178 to 126).

In further studies, five out of six human subjects lost weight when administered a composition of the invention. FIG. 12 provides weight loss versus body mass index. Subjects with normal or low BMI responded less while subjects with higher BMI showed greater response.

6.16 Example 16

Compositions of the Inventioin Reduced Blood Levels in Humans

The instant example provides reduction in blood glucose levels of human subjects upon administration of a composition of the invention.

In one experiment, a subject ingested 15 ml (0.1 mg/ml) of a composition of the invention or a control on a separate day. After 30 minutes, the subject ingested 15 g sucrose. Blood glucose was monitored over 140 minutes. As shown in FIG. 13A, the composition of the invention significantly lowered the glucose spike following ingestion of the sucrose.

In a second experiment, a subject finished a meal. One hour following the meal, the subject ingested 15 ml (0.1 mg/ml) of a composition of the invention or a control on a separate day. Blood glucose was monitored for 140 minutes following ingestion of the composition or control. As shown in FIG. 13B, the subject's blood glucose returned to baseline faster following administration of the composition of the invention.

In a third experiment, the subject fasted overnight. Blood glucose was monitored for 240 minutes starting at 6:00 am. At 8:11 am, the subject ingested 15 ml (0.1 mg/ml) of a composition of the invention. As shown in FIG. 13C, the composition of the invention temporarily lowered the subject's baseline blood glucose level in the fasted state.

Thus, the compositions of the invention are capable of reducing a blood glucose spike following challenge with sucrose, are capable of accelerating the return of blood glucose to baseline following a meal and are capable of reducing baseline blood glucose levels, at least temporarily, in the fasted state.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating obesity in a subject in need thereof comprising the step of administering to the subject a composition comprising an effective amount of a zinc-charged, protease-digested protein and an acceptable carrier, excipient or diluent, wherein the protein is zinc-charged by removing bound ions from the protein by contacting the protein with an effective amount of a chelating agent sufficient to remove the bound ions, followed by contacting the protein with a sufficient amount of zinc ion, wherein the protein is selected from the group consisting of $\alpha$-2-HS-glycoprotein (AHSG), $\alpha$-1-acid glycoprotein (AAG), $\alpha$-1-antitrypsin (AAT), albumin, transferrin and alpha fetoprotein, and wherein the zinc-charged, protease-digested protein induces apoptosis of an adipocyte.

2. The method of claim 1, wherein said subject is a human and said effective amount of the zinc-charged, protease digested protein is at least 0.02 mg/kg of subject's body weight.

3. The method of claim 1, wherein said subject is a human and said effective amount of the zinc-charged, protease digested protein is up to 4 mg/kg of subject's body weight.

4. The method of claim 1, wherein said subject is a human and said effective amount of the zinc-charged, protease digested protein is between 0.02 mg/kg and about 4 mg/kg of subject's body weight.

5. The method of claim 1, wherein said subject is a human and said effective amount of the zinc-charged, protease digested protein is between 1 mg per day and about 400 mg per day.

6. The method of claim 1, wherein the composition comprises two protease-digested, zinc-charged proteins selected from α-2-HS-glycoprotein, α-1-acid glycoprotein, α-1-antitrypsin, albumin, transferrin and α-fetoprotein.

7. The method of claim 1, wherein the composition comprises three protease-digested, zinc-charged proteins selected from α-2-HS-glycoprotein, α-1-acid glycoprotein, α-1-antitrypsin, albumin, transferrin and α-fetoprotein.

8. The method of claim 1, wherein the protease-digested, zinc-charged protein is less than 10 kilodaltons.

9. The method of claim 1, wherein the protease-digested, zinc-charged protein is less than 3 kilodaltons.

10. The method of claim 1, wherein the composition comprises protein fragments substantially of a size less than 10 kilodaltons.

11. The method of claim 1, wherein the composition comprises protein fragments substantially of a size less than 3 kilodaltons.

12. A method of reducing weight gain or inducing weight loss in a subject in need thereof comprising the step of administering to the subject a composition comprising an effective amount of a zinc-charged, protease-digested protein and an acceptable carrier, excipient or diluent, wherein the protein is zinc-charged by removing bound ions from the protein by contacting the protein with an effective amount of a chelating agent sufficient to remove the bound ions, followed by contacting the protein with a sufficient amount of zinc ion, wherein the protein is selected from the group consisting of α-2-HS-glycoprotein (AHSG), α-1-acid glycoprotein (AAG), α-1-antitrypsin (AAT), albumin, transferrin and alpha fetoprotein, and wherein the zinc-charged, protease-digested protein induces apoptosis of an adipocyte.

13. The method of claim 12, wherein said subject is a human and said effective amount of the zinc-charged, protease digested protein is at least 0.02 mg/kg of subject's body weight.

14. The method of claim 12, wherein said subject is a human and said effective amount of the zinc-charged, protease digested protein is up to 4 mg/kg of subject's body weight.

15. The method of claim 12, wherein said subject is a human and said effective amount of the zinc-charged, protease digested protein is between 0.02 mg/kg and about 4 mg/kg of subject's body weight.

16. The method of claim 12, wherein said subject is a human and said effective amount of the zinc-charged, protease digested protein is between 1 mg per day and about 400 mg per day.

17. The method of claim 12, wherein the composition comprises two protease-digested, zinc-charged proteins selected from α-2-HS-glycoprotein, α-1-acid glycoprotein, α-1-antitrypsin, albumin, transferrin and α-fetoprotein.

18. The method of claim 12, wherein the composition comprises three protease-digested, zinc-charged proteins selected from α-2-HS-glycoprotein, α-1-acid glycoprotein, α-1-antitrypsin, albumin, transferrin and α-fetoprotein.

19. The method of claim 12, wherein the protease-digested, zinc-charged protein is less than 10 kilodaltons.

20. The method of claim 12, wherein the protease-digested, zinc-charged protein is less than 3 kilodaltons.

21. The method of claim 12, wherein the composition comprises protein fragments substantially of a size less than 10 kilodaltons.

22. The method of claim 12, wherein the composition comprises protein fragments substantially of a size less than 3 kilodaltons.

23. A method of treating overweight in a subject in need thereof comprising the step of administering to the subject a composition comprising an effective amount of a zinc-charged, protease-digested protein and an acceptable carrier, excipient or diluent, wherein the protein is zinc-charged by removing bound ions from the protein by contacting the protein with an effective amount of a chelating agent sufficient to remove the bound ions, followed by contacting the protein with a sufficient amount of zinc ion, wherein the protein is selected from the group consisting of α-2-HS-glycoprotein (AHSG), α-1-acid glycoprotein (AAG), α-1-antitrypsin (AAT), albumin, transferrin and alpha fetoprotein, and wherein the zinc-charged, protease-digested protein induces apoptosis of an adipocyte.

24. The method of claim 23, wherein said subject is a human and said effective amount of the zinc-charged, protease digested protein is at least 0.02 mg/kg of subject's body weight.

25. The method of claim 23, wherein said subject is a human and said effective amount of the zinc-charged, protease digested protein is up to 4 mg/kg of subject's body weight.

26. The method of claim 23, wherein said subject is a human and said effective amount of the zinc-charged, protease digested protein is between 0.02 mg/kg and about 4 mg/kg of subject's body weight.

27. The method of claim 23, wherein said subject is a human and said effective amount of the zinc-charged, protease digested protein is between 1 mg per day and about 400 mg per day.

28. The method of claim 23, wherein the composition comprises two protease-digested, zinc-charged proteins selected from α-2-HS-glycoprotein, α-1-acid glycoprotein, α-1-antitrypsin, albumin, transferrin and α-fetoprotein.

29. The method of claim 23, wherein the composition comprises three protease-digested, zinc-charged proteins selected from α-2HS-glycoprotein, α-1-acid glycoprotein, α-1-antitrypsin, albumin, transferrin and α-fetoprotein.

30. The method of claim 23, wherein the protease-digested, zinc-charged protein is less than 10 kilodaltons.

31. The method of claim 23, wherein the protease-digested, zinc-charged protein is less than 3 kilodaltons.

32. The method of claim 23, wherein the composition comprises protein fragments substantially of a size less than 10 kilodaltons.

33. The method of claim 23, wherein the composition comprises protein fragments substantially of a size less than 3 kilodaltons.

* * * * *